United States Patent [19]
Miwa et al.

[11] Patent Number: 5,279,300
[45] Date of Patent: Jan. 18, 1994

[54] NONCONTACT TYPE TONOMETER

[75] Inventors: Tetsuyuki Miwa; Masahiro Sugimura; Munehiro Nakao; Ken Ootsuki, all of Aichi, Japan

[73] Assignee: Nidek Co., Ltd., Aichi, Japan

[21] Appl. No.: 827,610

[22] Filed: Jan. 29, 1992

[30] Foreign Application Priority Data

Jan. 30, 1991 [JP] Japan .................... 3-029415

[51] Int. Cl.⁵ ............................. A61B 3/16
[52] U.S. Cl. ............................. 128/648
[58] Field of Search ............ 128/645, 648, 652

[56] References Cited

U.S. PATENT DOCUMENTS

| | | | |
|---|---|---|---|
| 3,585,849 | 6/1971 | Grolman | 73/80 |
| 5,002,056 | 3/1991 | Takahashi et al. | 128/648 |
| 5,107,851 | 4/1992 | Yano et al. | 128/648 |

FOREIGN PATENT DOCUMENTS

63-300740 12/1988 Japan.

*Primary Examiner*—Randy C. Shay
*Attorney, Agent, or Firm*—Finnegan, Henderson, Farabow, Garrett & Dunner

[57] ABSTRACT

A noncontact type tonometer comprising with a nozzle for directing fluid into a cornea of a patient's eye and for deforming the cornea from a normally convex state, through a flat state, to a concave state, a detector for detecting fluid pressure within the nozzle and for generating pressure data corresponding to the fluid pressure, an optical detector for optically detecting corneal deformation and for generating optical data corresponding to a deformation state from the normally convex state to the concave state, a generator for generating predetermined time interval data according to a predetermined time interval, a clock, cooperable with the optical detector for optically detecting corneal deformation, for detecting an elapsed time interval for the cornea to deform to the flat state from the normally convex state and for generating elapsed time interval data corresponding thereto, a predictor for predicting an optimal time interval for the cornea to deform from the normally convex state to the flat state based upon the optical data and the predetermined time interval data and for generating optimal time interval data corresponding thereto, a comparator for comparing the elapsed time interval data with a predetermined range of the optimal time interval data, a pressure calculator for calculating the fluid pressure according to the pressure detected by the detector for detecting fluid pressure at the elapsed time interval where the cornea deforms to a flat state if the elapsed time interval lies within the predetermined range of the optimal time interval, and a controller for driving the nozzle.

16 Claims, 7 Drawing Sheets

NONCONTACT TYPE TONOMETER

BACKGROUND OF THE INVENTION

1. Field of the Invention

The present invention relates to a noncontact type tonometer by which intraocular pressure of a patient's eye is measured without contacting the eye by directing a compressed air pulse into the cornea of the patient's eye and deforming the cornea in a predetermined manner.

More particularly, the present invention relates to a noncontact type tonometer in which intraocular pressure of the patient's eye can be precisely measured without giving discomfort to the patient by predicting the ideal pressure value of the compressed air used to measure the intraocular pressure based on a predetermined condition of the cornea and the deformation of the cornea by compressed air with the predicted pressure value.

2. Description of the Related Art

Conventionally, two types of tonometers for measuring intraocular pressure of the patient's eye are known. One type is a traditional contact type tonometer and the other type is a noncontact type tonometer. The contact type tonometer has mechanical plunger which is placed in direct contact with the cornea to measure resistance of the patient's eyeball to deformation. This kind of contact type tonometer is not widely used at present because excessive compressed air pressure is directed to the cornea of the patient's eye. As a result, the patient experiences considerable discomfort.

A typical noncontact type tonometer is disclosed in U.S. Pat. No. 3,585,849. In this tonometer, an air pulse is directed to the cornea of the patient's eye in order to deform the cornea from its normal convex shape, through a flat shape, to a concave shape and vice versa. During this deformation, the deformation state of the cornea is observed as a function of time through the detection of a quantity of light reflected from the cornea. The light from a light source is reflected from the cornea. As a result, intraocular pressure of the patient's eye is measured based on the detected time elapsed until the cornea becomes flatshaped.

However, the aforementioned noncontact tonometer has a defect in that an excessive amount of compressed air may be directed to the cornea unnecessarily because there is no pressure control over the compressed air.

To improve this defect, a tonometer is provided in which the maximum pressure of the compressed air can be arbitrarily set in one of a plurality ranges as disclosed in Japanese patent application, laid-open No. 63-300740. According to the apparatus, based on information of the intraocular pressure of a patient's eye obtained after first measurement, the maximum pressure of the compressed air necessary for a second measurement can be selected. Thus, it is possible that only the compressed air pressure necessary for measuring intraocular pressure can be directed to the cornea of the patient's eye in the above improved apparatus by selecting the maximum pressure of the compressed air.

However, a control circuit for accomplishing the selection of one of the plurality of ranges becomes very complicated because such selection is conducted by controlling the electric current input of a solenoid which drives a piston through a division of a resistor in a control circuit.

Further, it is very difficult to judge whether or not the selected maximum pressure of compressed air is optimum to measure the intraocular pressure because this apparatus cannot respond to a change of the intraocular pressure due to a pulsation of the patient's eye, a change of atmospheric pressure, a delicate alignment deviation of elements of the device in the apparatus, etc. since the maximum pressure is directly selected based on the measured intraocular pressure.

Therefore, though the range of pressures is divided into more discrete units, the greater the variety of maximum pressures which may be applied. On the other hand, inferior measurement tends to occur due to lack of adequate pressure.

SUMMARY OF THE INVENTION

Accordingly, it is an object of the present invention to overcome the above mentioned problems and to provide a noncontact type tonometer in which the necessary and minimum ideal pressure of compressed air to measure intraocular pressure of the patient's eye can be automatically calculated based on various data measured according to a predetermined condition, thereby, precise measurement of intraocular pressure is accomplished without giving excessive discomfort to the patient.

According to the present invention and by its simple construction, the optimum pressure of the compressed air can be obtained without directing unnecessary pressure to the cornea of the patient's eye.

Precise data of intraocular pressure can be obtained with great reliability without giving excessive discomfort to the patient during measurement because intraocular pressure of the patient's eye is measured in good condition mentioned above. Further, precise measurement of intraocular pressure can be accomplished by simple operation of the apparatus without being dominated by or requiring the technique or skill of the oculist.

Thus, it is an object of the present invention to provide a noncontact type tonometer comprising means for directing fluid into a cornea of a patient's eye and for deforming the cornea from a normally convex state, through a flat state, to a concave state, means for detecting fluid pressure within the means for directing fluid and for generating pressure data corresponding to the fluid pressure, means for optically detecting corneal deformation and for generating optical data corresponding to a deformation state from the normally convex state to the concave state, means for generating predetermined time interval data according to a predetermined time interval, means cooperable with the means for optically detecting corneal deformation for detecting an elapsed time interval for the cornea to deform to the flat state from the normally convex state and for generating elapsed time interval data corresponding thereto, means for predicting an optimal time interval for the cornea to deform from the normally convex state to the flat state based upon the optical data and the predetermined time interval data and for generating optimal time interval data corresponding thereto, means for comparing the elapsed time interval data with a predetermined range of the optimal time interval data, means for calculating the fluid pressure according to the pressure detected by the means for detecting pressure at the elapsed time interval where the cornea deforms to a flat state if the elapsed time interval lies within the predetermined range of the optimal time interval, and control means for driving the fluid directing means. The above and further objects and novel features of the invention will more fully appear from the following detailed description when the same is read in connection with the accompanying drawings. It is to be expressly understood, however, that the drawings are for purpose of illustration only and not intended as a definition of the limits of the invention.

BRIEF DESCRIPTION OF THE DRAWINGS

The invention will be described with reference to the following drawings, wherein.

DETAILED DESCRIPTION OF THE PREFERRED EMBODIMENT

A detailed description of the first preferred embodiment of a noncontact type tonometer embodying the present invention will now be given with reference to the accompanying drawings.

Figure 1:
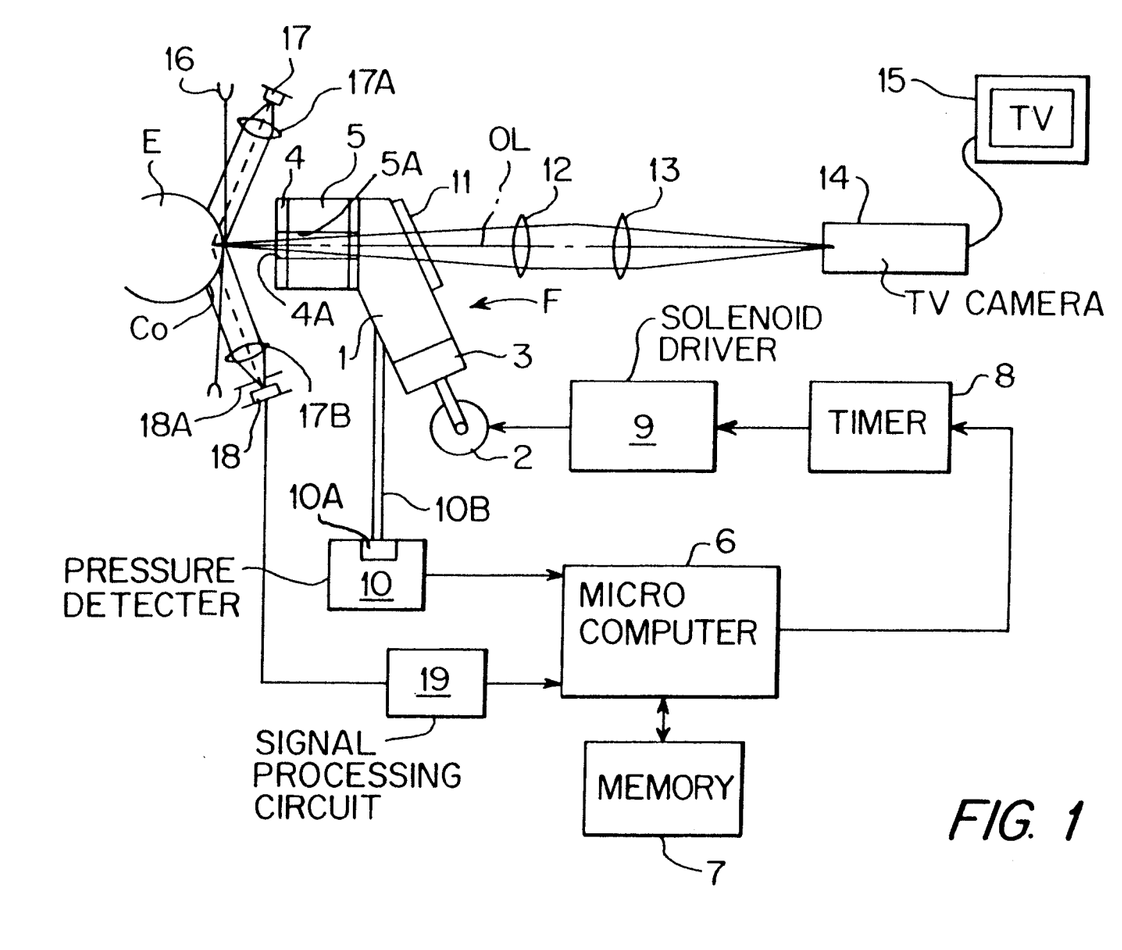
FIG. 1 is a block diagram which shows an optical system and a control system for directing compressed air to the cornea.

In FIG. 1, a device F for directing compressed air to a cornea CO of a patient's eye E is constructed from a cylinder 1 and a piston 3 slidably arranged in the cylinder 1 and further connected to a rotary solenoid 2. To the left-hand part (in reference to the Figure) of the cylinder 1 in FIG. 1, a nozzle 5, in which a nozzle hole 5A is formed, is attached. A window plate 4, in which a window part 4A is formed, is attached in front of the nozzle 5. The window plate 4 is arranged toward the cornea CO of the patient's eye E. In the window plate 4, the window part 4A, corresponding to the light path of luminous flux for positioning thereof, is made of clear glass.

Accordingly, air, which is compressed in the cylinder 1 by the piston 3 that is activated by the driven rotary solenoid 2, is directed to the cornea CO of the patient's eye E through both the nozzle hole 5A of the nozzle 5 and the window part 4A of the window plate 4.

Here, it can be understood that a linear motor having a reaction rail and a slider may also be used in this tonometer instead of the rotary solenoid 2.

A control system for the air directing device F mentioned above is described hereinafter. Control of the air directing device F is conducted by a microcomputer circuit 6 having CPU, ROM and RAM. The CPU calculates various data based on the air directing control program and various equations (later mentioned) stored in the ROM. The CPU then temporarily stores the calculated results in the RAM. Further, a memory 7 is connected to the microcomputer circuit 6 for storing various data measured from the predetermined condition of the cornea (later mentioned) and other measured parameters at that time.

To the microcomputer circuit 6, a timer 8 is connected. A solenoid driving circuit 9 is connected between the timer 8 and the rotary solenoid 2. Thus, when the rotary solenoid 2 is driven, the microcomputer circuit 6 sets the solenoid driving time (setting of the driving time is later mentioned) to the timer 8, thereby, the solenoid driving circuit 9 drives the rotary solenoid 2 during the solenoid driving time set to the timer 8.

Figure 2A:
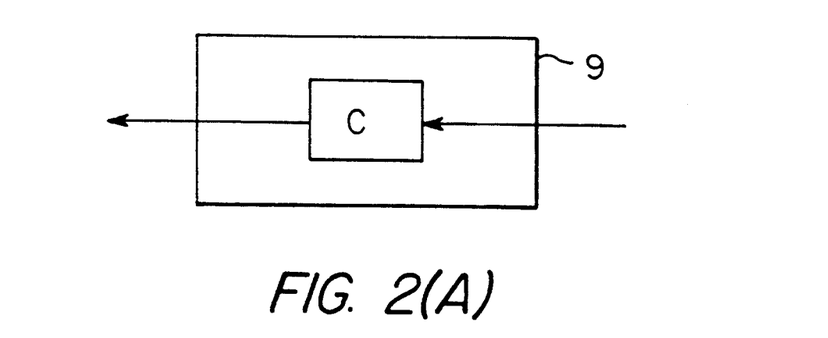
FIG. 2(A) is a block diagram of the solenoid driving circuit which uses condenser charging control circuit.

For controlling the solenoid driving time, a condenser charging control circuit C shown in FIG. 2(A) can be applied. A condenser is installed in the condenser charging control circuit C and the charging time of the condenser is variably changed according to the solenoid driving time set to the timer 8. Thereby, the solenoid driving time is controlled by electric energy applied to the rotary solenoid 2.

Figure 2B:
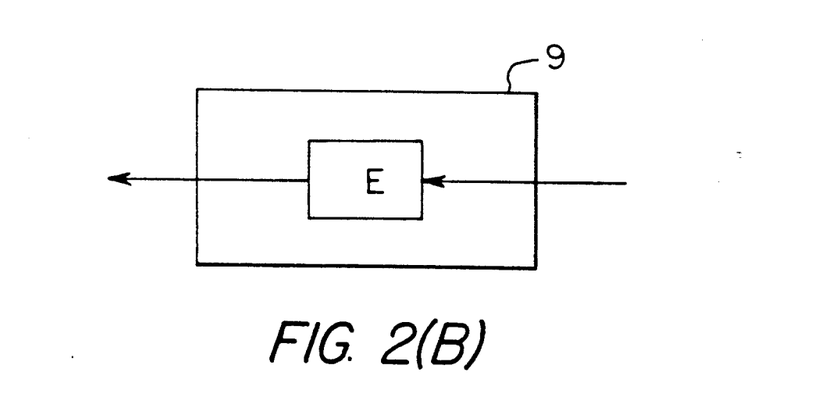
FIG. 2(B) is a block diagram of solenoid driving circuit which uses the control circuit for controlling the voltage application time.

The solenoid driving time can be controlled by a control circuit E for controlling voltage applying time shown in FIG. 2(B). In the control circuit E, the voltage applying time to the rotary solenoid 2 is variably changed by a switching circuit installed therein. Thereby, the solenoid driving time is controlled.

Figure 2C:
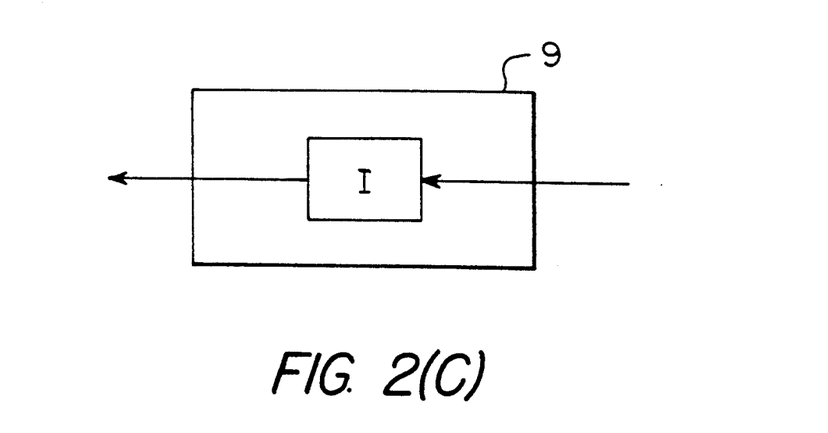
FIG. 2(C) is a block diagram of solenoid driving circuit which uses the control circuit for controlling the application time of an electric current.

Further, the solenoid driving time may be controlled by a control circuit I for controlling the applying time of an electric current. In the control circuit I, the applying time of an electric current to the rotary solenoid 2 is variably changed by a switching circuit installed therein. Thereby, the solenoid driving time is controlled.

A pressure detecting circuit 10 is connected to the cylinder 1, and this pressure detecting circuit 10 has a pressure sensor 10A which continuously detects the pressure of the compressed air in the cylinder 1 according to the compression of the air by the piston 3. The pressure sensor 10A outputs the detected pressure data to the microcomputer circuit 6. Here, the pressure sensor 10A can be arranged anywhere in the cylinder 1, though it is arranged through the end part of the nozzle 10B extending from the cylinder 1 in this embodiment.

Next, the optical system of the tonometer will be described. The optical axis OL passing through center of the cornea CO coincides with the screening optical path in order to screen a front image of the patient's eye E. At a part of the cylinder 1, through which the screening optical path passes, a clear glass plate 11 is arranged. An objective lens 12, an image formation lens 13 and T.V. camera 14 sensitive to the light in the near infrared range are aligned on the optical axis OL.

Figure 6:
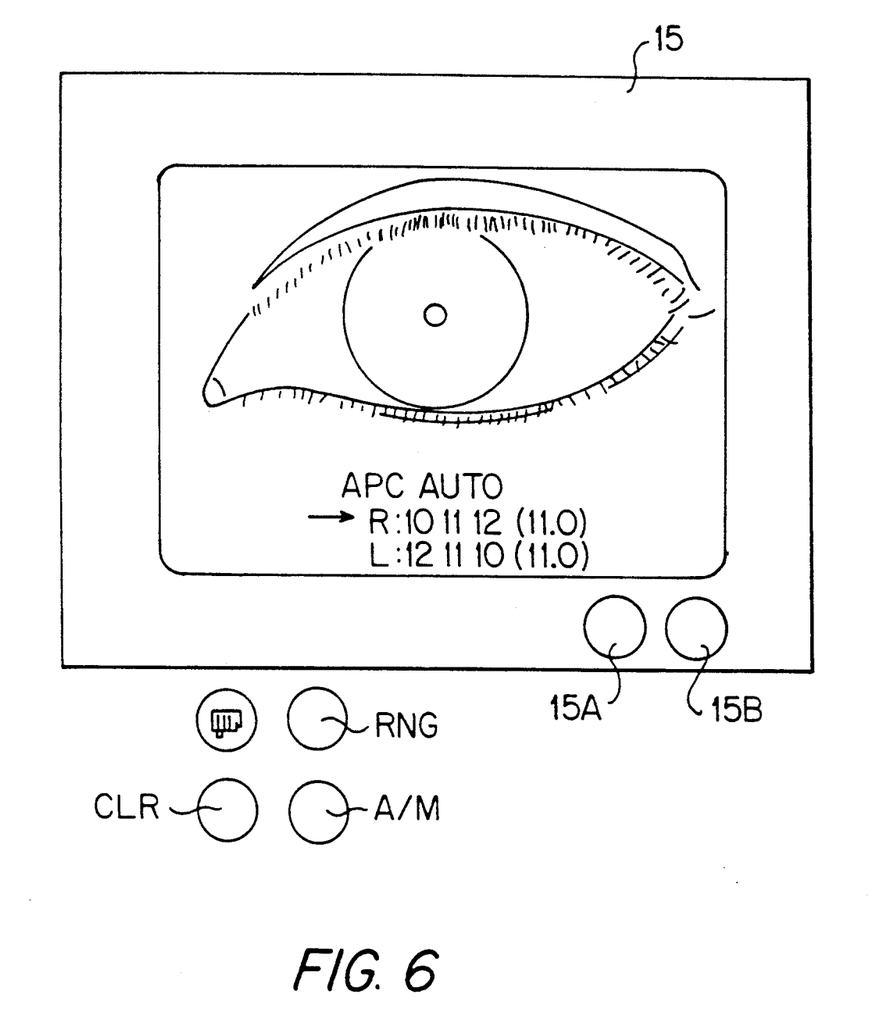
FIG. 6 is a representation of a T.V. monitor.

A half mirror (not shown but well-known in the art) is arranged between the clear glass plate 11 and the T.V. camera 14. Thus, according to this half mirror, the optical axis of the screening light path forming the Purkinje image is made coaxial with the optical axis OL. A T.V. monitor 15 is connected to the T.V. camera 14 and, on the T.V. monitor 15, the front image of the patient's eye E, taken by the T.V. camera 14, and the measured result of the intraocular pressure are displayed as shown in FIG. 6.

Further, two selection switches 15A and 15B are arranged on the T.V. monitor 15. The switch 15A is for changing between two measuring modes of the intraocular pressure of the eye E, one is the auto mode in which the intraocular pressure is automatically measured (in FIG. 6, the auto mode is shown). The other is the manual mode in which the intraocular pressure is, for example, measured on the condition that the compressed air pressure is set to 60 mm Hg or 30 mm Hg. The switch 15A, with each push thereof, alternately changes between both the auto mode and the manual mode. The switch 15B is an execution switch which is pushed after the intraocular pressure measurement mode has been selected and set by the switch 15A.

Numeral 16 designates a light source for irradiating the front part of the patient's eye E. Numeral 17 is a measuring light source which radiates near infrared light to the cornea CO for measuring the flat state of the cornea CO. The light emitted from the measuring light source 17 passes through an outgoing lens 17A and becomes a parallel luminous flux. Thereafter, the luminous flux, as a measuring light, is directed to the cornea CO. The measuring light that is reflected from the cornea CO is condensed by a condenser lens 17B and is directed to a photo detector 18 after passing through a pin hole 18A. Here, the photo detector 18 is arranged to such a position where a maximum light quantity can be obtained from the cornea CO when the cornea CO is applanated to a flat state. The photo detector 18 continuously detects incident light, and the optical data signal detected by the photo detector 18 is transmitted to the microcomputer circuit 6 through a signal processing circuit 19.

Here, a construction disclosed in the Japanese application laid-open No. 63-300740, in which a half mirror is arranged so as to become coaxial with a light path, can be used in the tonometer of the present invention, though various relations about the arranging position between the measuring light source 17 and the photo detector 18 and detecting method of the flat state of the cornea CO are proposed.

Next, the control method of directing the pressure of the compressed air to the cornea CO in the tonometer mentioned above is described.

Once the observer depresses the switch 15A and activates the auto mode, the microcomputer circuit 6 sets the predetermined time for driving the solenoid 2 to the timer 8. The solenoid driving circuit 9 drives the solenoid 2 during the time set to the timer 8. Thereby, the piston 3 compresses the air in the cylinder 1 and the compressed air is directed to the cornea CO through the nozzle 5. As a result, the cornea CO starts to applanate its shape and, according to applanation of the cornea CO, the optical data and the pressure data signal detected by the photo detector 18 and the pressure sensor 10A are continuously input into the microcomputer circuit 6 and processed thereby. The microcomputer circuit 6 conducts time processing according to the optical data and the pressure data input thereto. Further, it calculates the time corresponding to both the optical data and the pressure data. Graphs which show relations among the optical data, the pressure data and time data are shown in FIG. 3(A), (B) and (C).

Figure 3A:
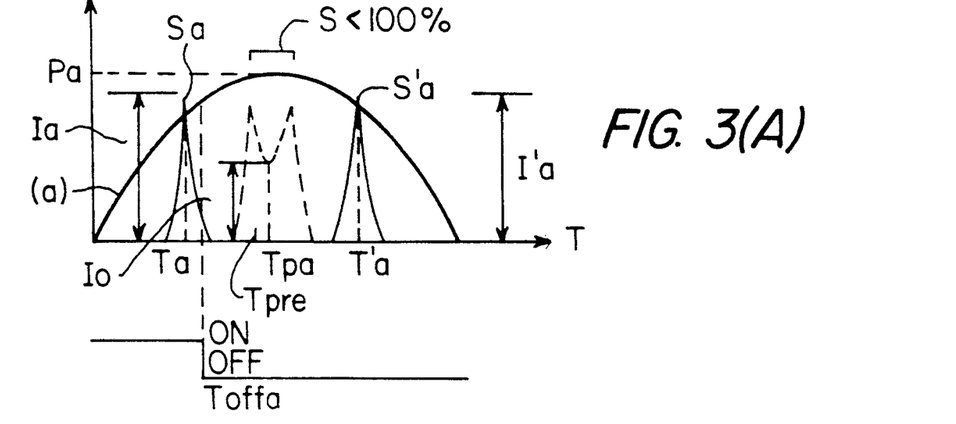
FIG. 3(A) is a graph which shows the changing state of luminous energy detected by a photo detector and the pressure of the compressed air detected by the pressure sensor as a function of time when the solenoid is stopped at a time Toffa.
Figure 3B:
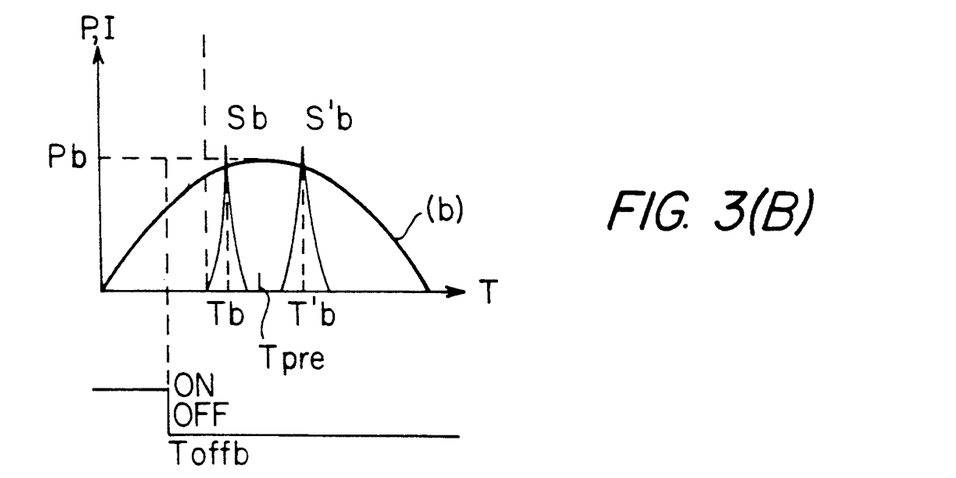
FIG. 3(B) is a graph which shows the changing state of luminous energy detected by the photo detector and the pressure of compressed air detected by the pressure sensor as a function of time when the solenoid is stopped at a time Toffb.
Figure 3C:
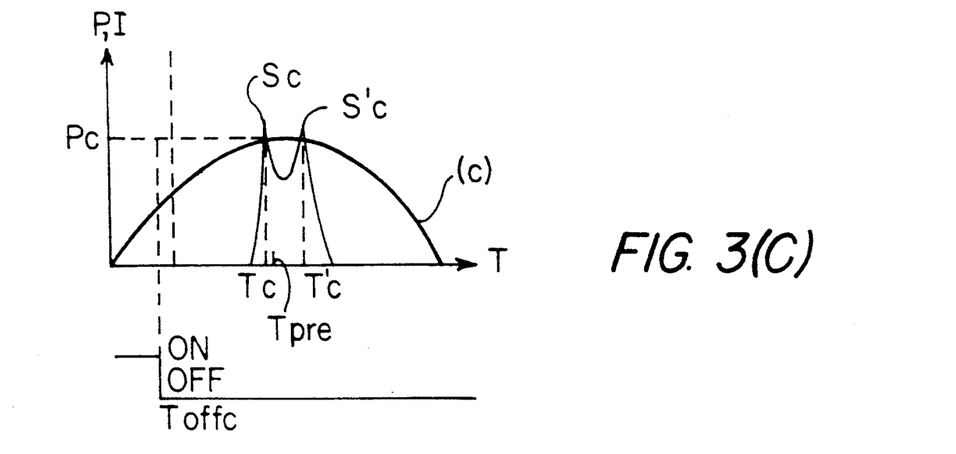
FIG. 3(C) is a graph which shows the changing state of the luminous energy detected by a photo detector and the pressure of compressed air detected by the pressure sensor as a function of time when the solenoid is stopped at a time Toffc.

In FIG. 3(A), the ordinate represents the light quantity I detected by the photo detector 18 and the pressure P ejected through the nozzle 5, and the abscissa represents the time T calculated by the microcomputer circuit 6. Clearly from FIG. 3(A), it can be understood that the cornea CO is gradually applanated from the normal convex state to the flat state while compressed air is directed to the cornea CO and that the light quantity detected by the photo detector 18 reaches maximum value Ia at the time Ta. After the maximum value Ia has been obtained, driving of the solenoid 2 is stopped at the time Toffa by the timer 8. On the other hand, the pressure curvature (a) continues to ascend because of the remaining stress in the solenoid 2 after the solenoid 2 is stopped. The maximum pressure Pa is observed at the time Tpa. The change in the quantity of light detected by the photo detector 18 is shown as a cornea applanation signal Sa in FIG. 3(A). The pressure P gradually descends after the maximum pressure Pa has been reached. Thus, the cornea applanation signal S'a can be obtained since the cornea CO gradually returns its natural form. Here, the light quantity detected by the photo detector 18 reaches a maximum value at time T'a.

Though the cornea applanation signals Sa, S'a, indicated with solid lines, are completely separated from each other as measured against the time axis (the abscissa) as shown in FIG. 3(A), the cornea applanation signals Sa, S'a are alternately indicated as broken lines shown in FIG. 3(A) in the case where they are incompletely separated as measured against the time axis. At this time, the light quantity at the time Tpa where the two cornea applanation signals are overlapping is defined Io. And the time data Ta, T'a, Tpa, the optical data Ia (Io) and the pressure data Pa are stored in the memory 7 as the data for calculating the solenoid driving time.

Calculation of the solenoid driving time is processed as follows. Here, equations mentioned hereinafter are stored in the ROM of the microcomputer circuit 6 and the CPU calculates the solenoid driving time based on such equations.

In this first embodiment, the solenoid driving time for controlling the solenoid 2 is calculated based on the splitting state of both the cornea applanation signals Sa, S'a. The splitting state is simply and effectively shown by using the light quantity Ia, Io and splitting fraction S as the index indicating the splitting state is given by the following equation (1).

$$S = [1 - (Io/Ia)] \times 100 (\%) \quad (1)$$

As may be understood from equation (1), the shorter difference between the time Ta and time T'a, the greater the light quantity Io and the smaller the splitting fraction S. Here, S=O means that the cornea applanation signals Sa, S'a are completely overlapped (Io=Ia) and S=100 (%) means that the cornea deformation signals Sa, S'a are completely separated from each other (Io=O). Further, when the cornea applanation signals are completely separated, it means that an excessive amount of compressed air is directed to the cornea CO, as a result, the cornea CO of the patient's eye E is exposed to the excessive compressed air. On the other hand, when the splitting fraction S becomes O, it means that the compressed air directed to the cornea CO is insufficient to applanate the cornea CO.

By the way, the ideal condition for directing the compressed air to the cornea CO is when the minimum air pressure by which the precise intraocular pressure is sufficiently detected can be obtained in spite of pulsation of the patient's eye, change of the atmospheric pressure, slight deviation of each device elements. Here, assumed that the splitting fraction is Sth when such minimum air pressure can be obtained, the splitting fraction S must satisfy the condition S≧St. As result of the inventors having conducted various experiments, it was proved that the most suitable value of the Sth is about 20 (Sth=20) in the tonometer of the first embodiment. Strictly speaking however, this Sth must be determined for every construction of each apparatus since the Sth may be different due to the construction of the individual apparatus.

Continuously, the suitable time Tpre elapsed until the cornea CO applanates to the flat state will be predicted. This time Tpre can be obtained by multiplying of the time Tpa, corresponding to the maximum pressure Pa through the time T'a, where the flat states of the cornea CO are detected and the splitting fraction. Correctly speaking, the time Tpa presently detected would substantially correspond to the time Tpa already detected, if taking the changed state of the intraocular pressure in measurement and adjusting method mentioned hereinafter into consideration, though the time Tpa is different according to the time at which the solenoid 2 is stopped, in case that the air pressure is controlled by the time at which the solenoid 2 is stopped as the first embodiment.

The Tpre can be obtained according to the following equation (2) when the splitting fraction S=100 (%), that is, the cornea applanation signals Sa, S'a are completely separated.

$$Tpre = Tpa \cdot \left[ 1 - \left( \frac{Tpa - Ta}{S(T'a - Ta)} \right) \cdot Sth \right] \quad (2)$$

Here, the amended value S' obtained by observing S, in taking the changing state that the cornea applanation signals Sa, S'a changes due to the shape of the cornea CO, etc. into consideration, can be substituted for the S in equation (2).

On the contrary, when the cornea applanation signals Sa, S'a are not completely separated (shown in the graph of FIG. 3(A) as broken lines) the Tpre is calculated by the following equation (3) in which factor of the Ta, T'a is omitted from the equation (2) because there is not an effective difference between Ta and T'a.

$$\text{for } S < 100, \text{ then } Tpre = Tpa - \left[ \left( \frac{Tpa - Ta}{S} \right) \cdot Sth \right] \quad (3)$$

Calculations according to the above equations (1), (2) and (3) are executed by the microcomputer circuit 6. In order to calculate the most suitable time Tpre, it is necessary to obtain the timer off time Toffb of the timer 8 (at that time, the solenoid 2 is stopped) shorter than the timer off time Toffa shown in FIG. 3(A).

When the cornea applanation signals Sa, S'a are separated, the amount of pressure increase as measured against the time component descends if the time at which the solenoid 2 is stopped is very short. Therefore, the time until the flat state of the cornea CO is detected is long. By investigating the relation between the time that the solenoid 2 is stopped and the time that the flat state of the cornea CO is detected, it is recognized that a relationship in reverse ratio can be found between them.

Accordingly, the relation among the Toffa, Toffb, Ta and Tpre is formed as represented by the following equation (4).

$$\text{Toffb/Toffa} = Ta/Tpre \quad (4).$$

Equation (4) is modified to the following equation (5) and the Toffb is obtained from equation (5).

$$Toffb = \frac{Ta}{Tpre} \cdot Toffa \quad (5)$$

According to equation (5), the microcomputer circuit 6 sets the Toffb to the timer 8 and drives the solenoid 2 through the solenoid driving circuit 9 based on the Toffb as driving control time for the solenoid 2 at next measurement of the intraocular pressure.

FIG. 3(B) shows a graph in which the cornea applanation signals Sb, S'b obtained when the solenoid 2 is stopped at the Toffb and the air pressure curve (b) detected by the pressure sensor 10A. If it is determined that the Tb obtained from the graph in FIG. 3(B), which corresponds to the cornea applanation signal Sb, is within the threshold range as measured against the Tpre (for instance, assuming that the Tb must be in ±10% range of the Tpre, Tpre×1.1≧Tb≧Tpre×0.9 must be satisfied), the pressure Pb according to the Tb in FIG. 3(B) becomes a suitable pressure value for the intraocular pressure of the patient's eye E. On the contrary, if it is determined that the Tb obtained is out of the threshold range as measured against the Tpre, the Toffb is amended again and the microcomputer circuit 6 calculates a third time Toffc at which the solenoid 2 is stopped. In this case, Toffc can be obtained by amending the time deviation between the Tpre and the Tb, thus, the Toffc can be simply calculated according to the following equation (6) by using equation (5).

$$Toffc = \frac{Tb}{Tpre} \cdot Toffb$$

Figure 4:
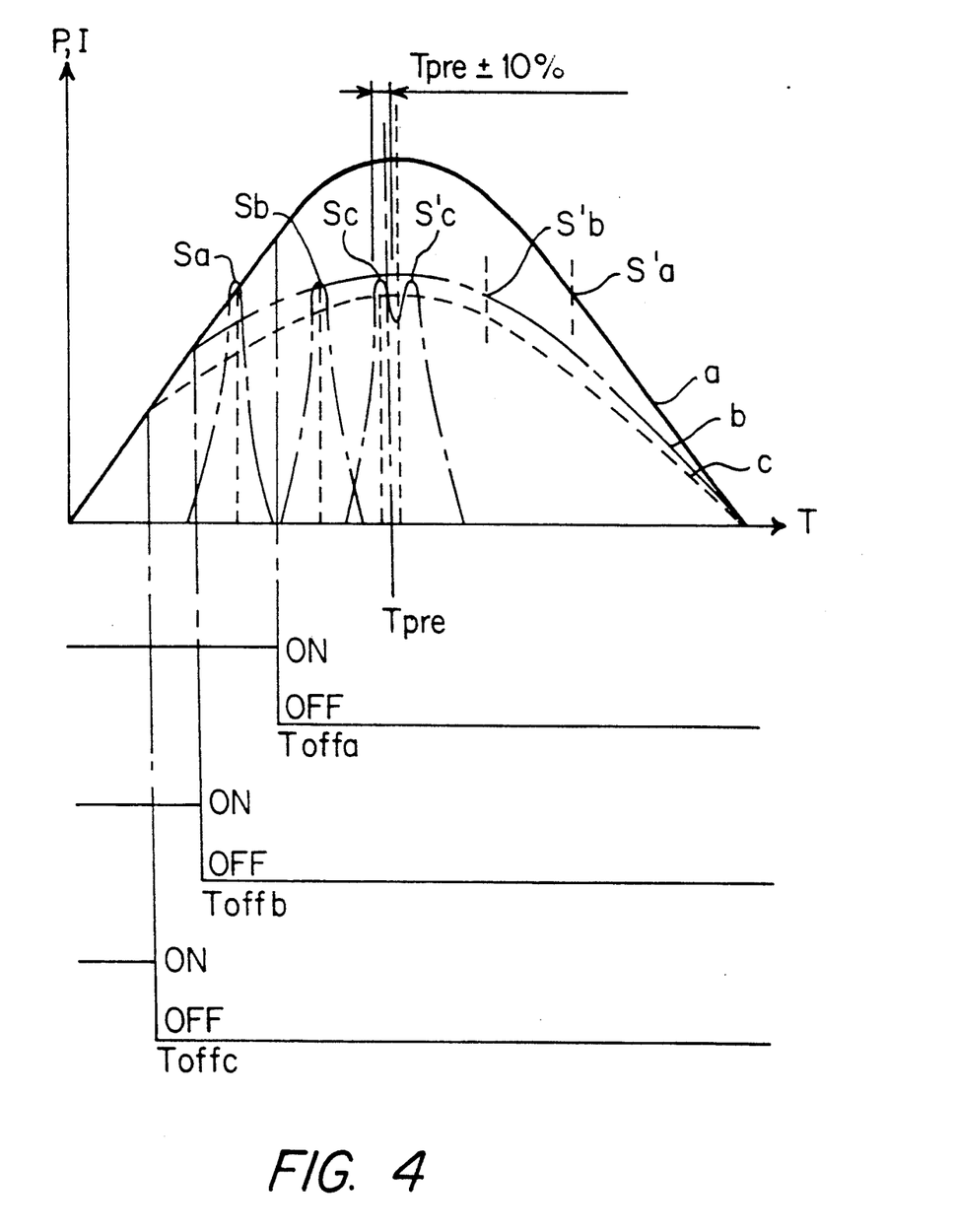
FIG. 4 is a graph which totally or collectively shows graphs in FIG. 3(A), FIG. 3(B) and FIG. 3(C)

FIG. 3(C) shows a graph in which the cornea applanation signals Sc, S'c are obtained when the solenoid 2 is stopped at the Toffc and the air pressure curve (c) is detected by the pressure sensor 10A. Further, FIG. 4 shows a graph in which the graphs shown in FIG. 3(A), (B) and (C) are combined (here, for convenience, the slight difference of the time Tpa yielded when measured is negated as mentioned above).

As shown in FIG. 3(C), the Tc at which the flat state of the cornea CO is detected, according to the Toffc, lies in the ±10% threshold range of the Tpre. At that time, the maximum air pressure Pc is suitable for the intraocular pressure measurement of the patient's eye E, taking into consideration various causes which change the intraocular pressure. Of course, in the case where the Ta is in the threshold range of Tpre (±10% of the Tpre), amending procedures according to equations (5) and (6) are not necessary.

Figure 5A:
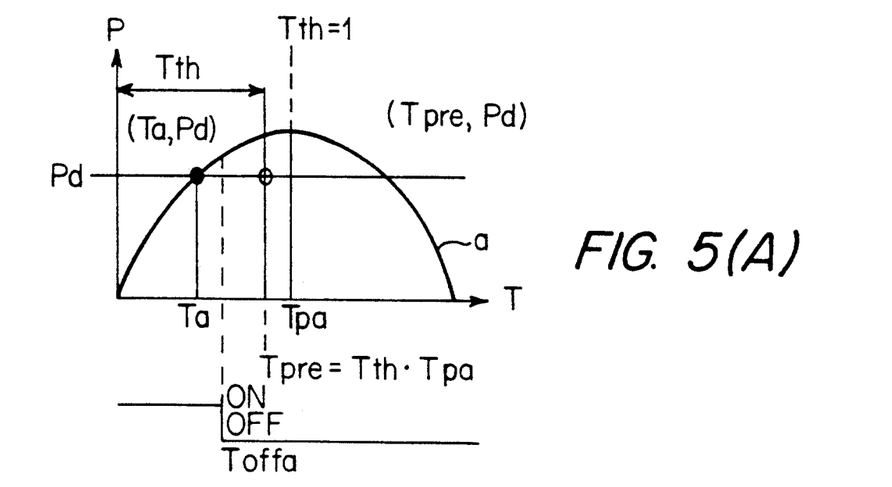
FIG. 5(A) is a graph which shows that the predicted optimum time for deforming the cornea is determined based on a threshold corresponding to the time in which the pressure of compressed air reaches a maximum value.

Next, the second embodiment of the present invention will be described in reference to FIG. 5. In this embodiment, the same apparatus is used as the first embodiment except for the method of calculation programmed into the microcomputer circuit 6. As shown in FIG. 5(A), the Tpre is based upon the threshold value Tth as is compared to the Tpa at which the maximum air pressure is detected. Tth can be calculated according to the following equation (7).

$$Tpre = Tth \cdot Tpa \text{ where Tth ranges from 0.0 to 1.0.} \quad (7)$$

It may be understood from FIG. 5(A) that the more Ta approaches Tpa, the lower the air pressure which need be applied for measurement of the intraocular pressure. However, in that case, it is possible that the air pressure sufficient to applanate the cornea CO cannot be obtained. Accordingly, the threshold value Tth must be decided taking the causes for changing the intraocular pressure into consideration, similarly to the threshold value Sth of the splitting fraction S in the first embodiment. On the basis of various experiments, it is found that the suitable value of the Tth in the second embodiment is about 0.9 (Tth=0.9).

Figure 5B:
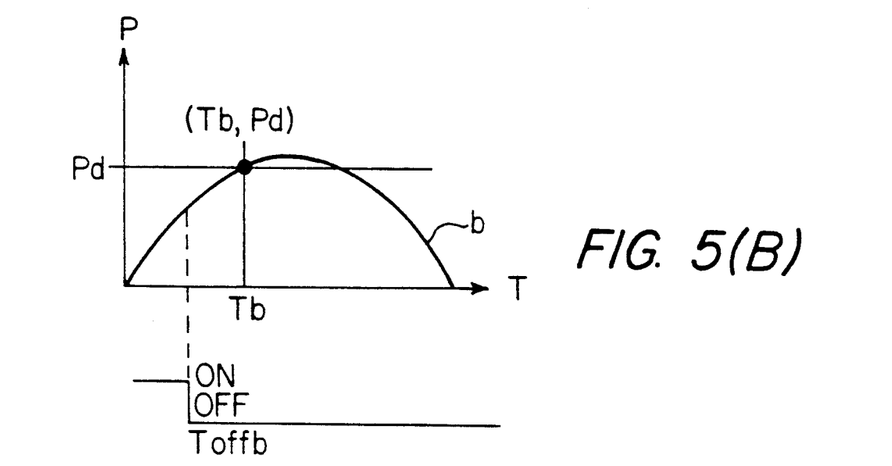
FIG. 5(B) is a graph which shows that the detected time is obtained by substituting the predicted optimum time into equation (5)
Figure 5D:
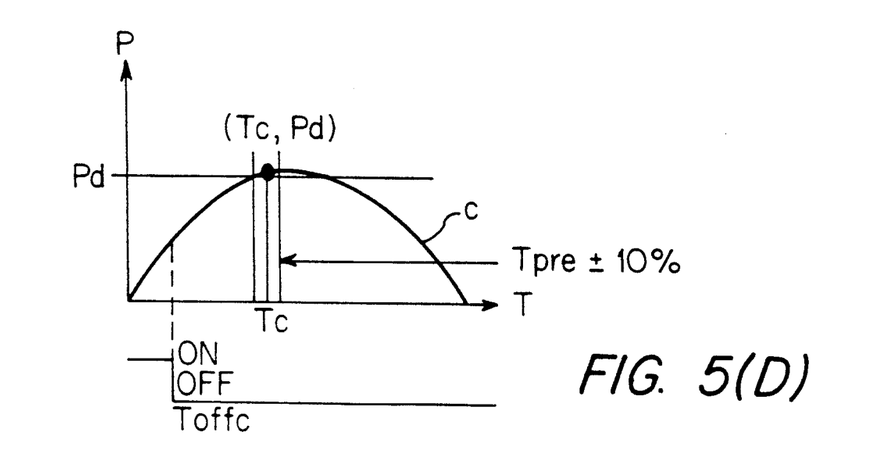
FIG. 5(C) is a graph which shows that the detected time is obtained by using equation (6) as an amending equation.

At the first measurement, the time Ta (corresponding pressure value is Pd), at which the flat state of the cornea CO is detected, and the time Tpa, at which point the air pressure reaches the maximum air pressure, are obtained. At this time, Toffa is set in the timer 8 as a control time. Based on the obtained Ta, Tpa, Toffa by the above measurement and the Tpre calculated through equation (7), the time Tb is measured at the second measurement by using the Toffb calculated from the equation (5) mentioned above.

If it is determined that the obtained Tb at which the flat state of the cornea CO is detected is not in the range of ±10% of the Tpre, the Tc is measured at the third measurement by using Toffc calculated according to equation (6) as mentioned above.

Figure 7A:
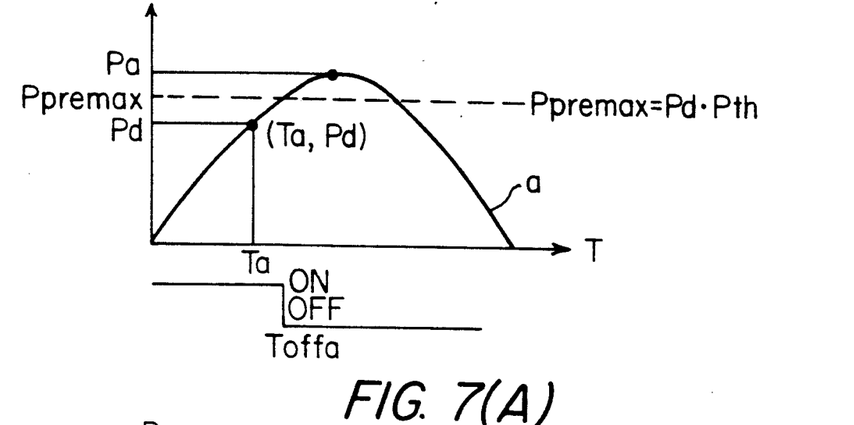
FIG. 7(A) is a graph which shows that the maximum pressure Ppremax optimum to deform the cornea is determined from the threshold value Pth, against the Pd through which the flat state of the cornea is detected.

Further, a third embodiment of the present invention will be described hereinafter, referring to FIG. 7. In this embodiment, the same apparatus is used as in the first embodiment except for calculation method by the microcomputer 6. As shown in FIG. 7(A), the maximum pressure Ppremax optimum to applanate the cornea CO is decided from following equation (8).

$$Ppremax = Pd \cdot Pth \text{ where Pth ranges from 1.0 to 1.2.} \quad (8)$$

Here, the Pd is the pressure through which the flat state of the cornea CO is detected as shown in FIG. 7(A), and the Pth is the threshold value as measured against the Pd. It may be understood from FIG. 7(A) that the closer the Pd approaches the maximum pressure Pa, the lower the air pressure that can be applied to measure the intraocular pressure.

However, in that case, it is possible that the air pressure sufficient to applanate the cornea CO cannot be obtained. Accordingly, the threshold value Pth must be decided in taking causes changing the intraocular pressure into consideration. This applies similarly to the threshold value Sth of the splitting fraction S in the first embodiment and to the threshold value Tth against the Tpa in the second embodiment. On the basis of the various experiments, it is found that the suitable value of the Pth is about 1.1.

At the first measurement, Pd and the maximum pressure Pa are measured as shown in FIG. 7(A). At that time, the solenoid driving time set to the timer 8 is the Toffa at which point the solenoid 2 is stopped.

Figure 7B:
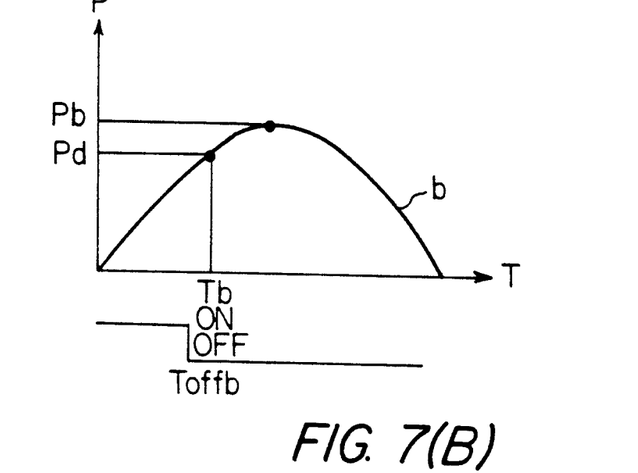
FIG. 7(B) is a graph which shows that the maximum pressure Pb is measured by using the Toffb calculated from equation (9)

Based on the Pd, the Pa, the Toffa obtained above and the Ppremax sufficient to obtain the Pd calculated from equation (8), the timer off time Toffb (shown in FIG. 7(B)), at which the timer 8 is stopped, is calculated.

Here, in order to calculate the Toffb, the following equation (9), which is derived based on the pressure value different from equation (5), is used.

$$Toffb = (Toffa \cdot Ppremax)/Pa \quad (9).$$

Equation (9) is derived from the following equation (10) in which the timer driving time Toffa, Toffb are related to the maximum pressure Pa.

$$\frac{Toffb}{Ppremax} = \frac{Toffa}{Pa} \quad (10)$$

At the second measurement, the maximum pressure Pb is measured as shown in FIG. 7(B) by controlling the solenoid 2 according to the Toffb calculated from equation (9). Further, it is determined whether or not the maximum pressure Pb is in the ±10% range of the Ppremax. If it is judged that the Pb is in the ±10% range of the Ppremax, Pb becomes the suitable pressure to applanate the cornea CO.

On the other hand, in case that the Pb is out of the ±10% range of the Ppremax, the Toffc used for the third measurement is calculated from the following equation (11) to amend the Toffb.

$$Toffc = (Toffb \cdot Ppremax)/Pb \quad (11).$$

Figure 7C:
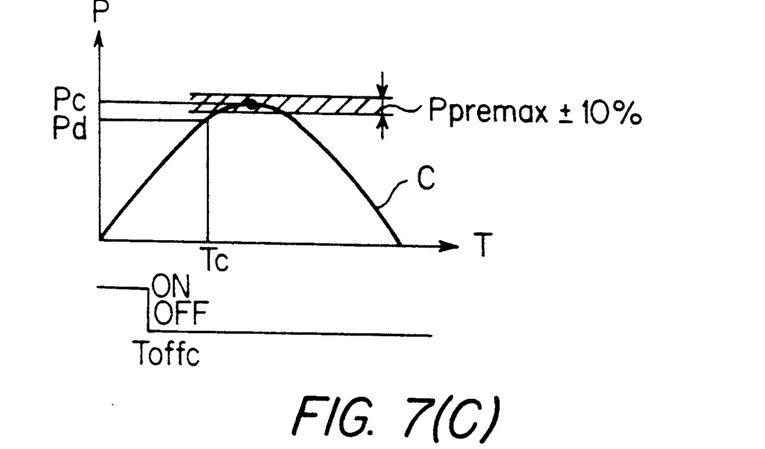
FIG. 7(C) is a graph which shows that the maximum pressure Pc measured by using the Toffc from equation (11) is judged in the predetermined range of the Ppremax.

At the third measurement, the maximum pressure Pc is measured as shown in FIG. 7(C) by controlling the solenoid 2 according to the Toffc calculated from equation (11). If it is judged that the maximum pressure Pc is in the ±10% range of the Ppremax, the Pc become the suitable pressure to applanate the cornea CO.

Finally, the intraocular pressure of the patient's eye E is calculated by using the data obtained through the first, the second and the third embodiments. The intraocular pressure can be indirectly obtained at every stopping of the solenoid 2 by calculating from an equation stored in the apparatus having the relationship between the time at which the flat state of the cornea CO is detected and the intraocular pressure. Such a method is well-known in the art as evidenced by the above-cited U.S. Pat. No. 3,585,849 issued to Grolman. Further, the intraocular pressure can be directly obtained by calculating with an equation which defines the relationship between the intraocular pressure and the pressure by which the flat state of the cornea CO is detected. Such calculation is well-known in the art as evidenced by the above-cited Japanese Patent Application, laid open, No. 63-30,0740.

Though above description relates to the intraocular pressure measured in the auto mode set by the mode changing switch 15A arranged on the T.V. monitor 15 and the measurement thereof is executed by the switch 15B, the intraocular pressure can be measured in the manual mode (where the air pressure can be selected from 60 mm Hg or 30 mm Hg) set by the switch 15A through execution of the switch 15B.

Here, the air pressure 60 mm Hg is used for the patient's eye E which has comparatively high intraocular pressure and the air pressure 30 mm Hg is used for the patient's eye E which has comparatively low intraocular pressure.

While the invention has been particularly shown and described with reference to preferred embodiments thereof, it will be understood by those skilled in the art that the foregoing and other changes in form and details can be made therein without departing from the spirit and scope of the invention. For instance, the present invention can be applied to the apparatus in which the maximum pressure of the compressed air can be set in plural stages by changing driving torque of the solenoid 2. In such apparatus, the driving torque suitable for the intraocular pressure measurement is selected by comparing the calculated value through the above equations according to a driving torque used with the air pressure value according to each driving torque stored in the apparatus.

What is claimed is:

1. A noncontact type tonometer comprising:
   means for directing fluid into a cornea of a patient's eye and for deforming the cornea from a normally convex state, through a flat state, to a concave state,
   means for detecting fluid pressure within the means for directing fluid and for generating pressure data corresponding to the fluid pressure,
   means for optically detecting corneal deformation and for generating optical data corresponding to a deformation state from the normally convex state to the concave state,
   means cooperable with the means for optically detecting corneal deformation for detecting a first elapsed time interval for the cornea to deform to the flat state from the normally convex state and for generating first elapsed time interval data corresponding thereto,
   means for detecting a second elapsed time interval until the means for detecting fluid pressure detects a maximum fluid pressure and for generating second elapsed time interval data corresponding thereto,
   means for predicting an optimal time interval for the cornea to deform from the normally convex state to the flat state based upon the optical data, the first and the second elapsed time interval data and for generating optimal time interval data corresponding thereto,
   means for comparing the first elapsed time interval data with a predetermined range of the optimal time interval data,
   means for determining the maximum fluid pressure detected by the means for detecting fluid pressure as an optimal fluid pressure to be provided to the means for directing fluid, if the first elapsed time interval lies within the predetermined range of the optimal time interval, and
   control means for driving the fluid directing means.

2. The noncontact type tonometer according to claim 1, further comprising memory means within the control means for storing the pressure data generated by the means for detecting fluid pressure, the optical data generated by the means for detecting corneal deformation, and the first and the second elapsed time interval data, and wherein the predicting means determines the optimal time interval according to the optical data, the first and the second elapsed time interval data.

3. The noncontact type tonometer according to claim 1, further comprising means for calculating driving time of the means for directing fluid based on the first elapsed time interval data generated by the means for detecting a first elapsed time interval and the optimal time interval data predicted by the predicting means.

4. The noncontact type tonometer according to claim 3, wherein the means for determining the maximum fluid pressure further includes means for changing the maximum fluid pressure according to the driving time calculated by the means for calculating the driving time.

5. The noncontact type tonometer according to claim 4, further comprising timer means to which the driving time is coordinated and wherein the control means controls the means for directing fluid according to the driving time.

6. The noncontact type tonometer according to claim 3, wherein the means for directing fluid comprises:
   a cylinder,
   a piston slidably arranged in the cylinder,
   a solenoid connected to the piston, and
   wherein the control means controls the solenoid according to the driving time calculated by the means for calculating driving time.

7. The noncontact type tonometer according to claim 6, further comprising a solenoid driving circuit for driving the solenoid according to the driving time.

8. The noncontact type tonometer according to claim 7, further comprising a condenser connected to the solenoid driving circuit and charged by the solenoid driving circuit according to the driving time.

9. The noncontact type tonometer according to claim 7, wherein the solenoid driving circuit controls a voltage or an electric current applied to the solenoid according to the driving time.

10. The noncontact type tonometer according to claim 1, wherein the means for directing fluid deforms the cornea through a first deforming state in which the cornea deforms from the normally convex shape through the flat shape to a concave shape and then through a second deforming state in which the cornea deforms from the concave shape through the flat shape to the normally convex shape,
   the means for optically detecting corneal deformation optically detects the first and second deforming states of the cornea, and
   the means for predicting the optimal time interval predicts the optimal time interval according to the first elapsed time interval for the cornea to deform to the flat state during each of the first and second deforming states.

11. The noncontact type tonometer according to claim 1, further comprising means for adjusting the first time interval data generated by the means for detecting a first elapsed time interval so as to be in the predetermined range of the optimal time interval predicted by the means for predicting the optimal time interval if the first elapsed time interval is not in the predetermined range of the optimal time interval.

12. A noncontact type tonometer comprising:

means for directing fluid into a cornea of a patient's eye and for deforming the cornea from a normally convex state, through a flat state, to a concave state, means for detecting fluid pressure within the means for directing fluid and for generating pressure data corresponding to the fluid pressure, means for optically detecting corneal deformation and for generating optical data corresponding to a deformation state from the normally convex state to the concave state, means cooperable with the means for optically detecting corneal deformation for detecting a first elapsed time interval for the cornea to deform to the flat state from the normally convex state and for generating first elapsed time interval data corresponding thereto, means for detecting a second elapsed time interval until the means for detecting fluid pressure detects a maximum fluid pressure and for generating second elapsed time interval data corresponding thereto, memory means for storing the pressure data, the optical data, the first and the second elapsed time interval data, means for predicting an optimal time interval for the cornea to deform from the normally convex state to the flat state based upon the optical data, the first and the second elapsed time interval data stored in the memory means and for generating optimal time interval data corresponding thereto, means for comparing the first elapsed time interval data with a predetermined range of the optimal time interval data, means for determining the maximum fluid pressure detected by the means for detecting fluid pressure as an optimal fluid pressure to be provided to the means for directing fluid, if the first elapsed time interval lies within the predetermined range of the optimal time interval, and control means for controlling the means for directing fluid based on the optimal fluid pressure in accordance with the optimal fluid pressure.

13. The noncontact type tonometer according to claim 12, further comprising means for displaying the optimal fluid pressure set by the means for setting an optimal fluid pressure, and means arranged on the means for displaying the optimal fluid pressure for selecting one of a first mode in which the optimal fluid pressure is automatically determined and a second mode in which the optimal fluid pressure is manually determined.

14. A noncontact type tonometer comprising:

means for directing fluid into a cornea of a patient's eye and for deforming the cornea from a normally convex state, through a flat state, to a concave state, means for detecting fluid pressure within the means for directing fluid and for generating pressure data corresponding to the fluid pressure, means for optically detecting corneal deformation and for generating optical data corresponding to a deformation state from the normally convex state to the concave state, means cooperable with the means for optically detecting corneal deformation for detecting a first elapsed time interval for the cornea to deform to the flat state from the normally convex state and for generating first elapsed time interval data corresponding thereto, means for detecting a second elapsed time interval until the means for detecting fluid pressure detects a maximum fluid pressure and for generating second elapsed time interval data corresponding thereto, means for predicting an optimal time interval for the cornea to deform from the normally convex state to the flat state based upon the second elapsed time interval data and for generating optimal time interval data corresponding thereto, means for judging if the first elapsed time interval is in a predetermined range of the optimal time interval predicted by the means for predicting the optimal time interval, means for determining a fluid pressure corresponding to the first elapsed time interval detected by the means for detecting fluid pressure as an optimal fluid pressure to be provided to the means for directing fluid, when the judging means determines that the first elapsed time interval is within the predetermined range of the optimal time interval, calculating means for calculating a pressure control condition of the means for directing fluid when the judging means determines that the first elapsed time interval is not within the predetermined range of the optimal time interval by adjusting the first elapsed time interval data closely to the optimal time interval, and means for controlling the means for directing fluid according to the pressure control condition.

15. A noncontact type tonometer comprising:

means for directing fluid into a cornea of a patient's eye and for deforming the cornea from a normally convex state, through a flat state, to a concave state, means for optically detecting corneal deformation and for generating optical data corresponding to a deformation state from the normally convex state to the concave state, means for detecting fluid pressure within the means for directing fluid and for generating pressure data corresponding to the fluid pressure, first means cooperable with the means for optically detecting corneal deformation for detecting a first fluid pressure when the flat state of the cornea is detected by the means for optically detecting corneal deformation and generating first fluid pressure data corresponding thereto, second means for detecting a maximum fluid pressure in cooperation with the means for detecting fluid pressure and for generation maximum fluid pressure data corresponding thereto, means for predicting an optimal fluid pressure based on the first fluid pressure detected by the first means, means for judging whether the maximum fluid pressure is within a predetermined range of the optimal fluid pressure, means for determining the maximum fluid pressure as the optimal fluid pressure to be provided to the means for directing fluid, when the judging means determines that the maximum fluid pressure is within the predetermined range of the optimal fluid pressure, means for calculating a pressure control condition of the means for directing fluid when the judging means determines that the maximum fluid pressure is not within the predetermined range of the optimal fluid pressure by adjusting the maximum fluid pressure closely to the optimal fluid pressure, and means for controlling the means for directing fluid according to the pressure control condition calculated by the means for calculating a pressure control condition.

16. A control system utilized in a noncontact type tonometer wherein the tonometer comprises:

means for directing fluid into a cornea of a patient's eye and for deforming the cornea from an normally convex state, through a flat state, to a concave state, means for detecting fluid pressure within the means for directing fluid and for generating pressure data corresponding to the fluid pressure, means for optically detecting corneal deformation and for generating optical data corresponding to a deformation state from the normally convex state to the concave state, means cooperable with the means for optically detecting corneal deformation for detecting a first elapsed time interval for the cornea to deform to the flat state from the normally convex state and for generating first elapsed time interval data corresponding thereto, and means for detecting a second elapsed time interval until the means for detecting fluid pressure detects a maximum fluid pressure and for generating second elapsed time interval data corresponding thereto, wherein the control system comprises:

means for predicting an optimal time interval for the cornea to deform from the normally convex state to the flat state based upon the optical data and the first and the second elapsed time interval data and for generating optimal time interval data corresponding thereto, means for judging if the first elapsed time interval is in a predetermined range of the optimal time interval predicted by the means for predicting the optimal time interval, calculating means for calculating a pressure control condition of the means for directing fluid when the judging means determines that the first elapsed time interval is not within the predetermined range of the optimal time interval by adjusting the first elapsed time interval data closely to the optimal time interval, and means for controlling the means for directing fluid according to the pressure control condition.

* * * * *

UNITED STATES PATENT AND TRADEMARK OFFICE
CERTIFICATE OF CORRECTION

PATENT NO. : 5,279,300
DATED : January 18, 1994
INVENTOR(S) : Tetsuyuki Miwa et al.

It is certified that error appears in the above-indentified patent and that said Letters Patent is hereby corrected as shown below:

On title page: Item [75]    change "Ken" to --Kan--. *

Claim 10, Column 13, Line 1, after "interval" insert --data--. *

Claim 15, Column 14, Line 67, change "generation" to --generating--.

Signed and Sealed this

Tenth Day of January, 1995

Attest:

BRUCE LEHMAN

Attesting Officer    Commissioner of Patents and Trademarks